United States Patent [19]

Noffsinger et al.

[11] Patent Number: 5,719,053

[45] Date of Patent: Feb. 17, 1998

[54] CHROMATOGRAPHIC METHOD FOR THE IDENTIFICATION AND CHARACTERIZATION OF HEMOGLOBIN VARIANTS IN BLOOD

[75] Inventors: Jimmie K. Noffsinger, Overland Park, Kans.; Ching-Nan Ou, Houston, Tex.

[73] Assignee: Primus Corporation, Kansas City, Mo.

[21] Appl. No.: 642,175

[22] Filed: May 6, 1996

[51] Int. Cl.$^6$ .................................................. G01N 33/72
[52] U.S. Cl. ............................................ 435/288.6; 436/66
[58] Field of Search .................... 435/6, 288.6; 436/66

[56] References Cited

U.S. PATENT DOCUMENTS

| | | | |
|---|---|---|---|
| 4,264,605 | 4/1981 | Dean et al. | |
| 4,371,374 | 2/1983 | Cerami et al. | 422/61 |
| 4,409,335 | 10/1983 | Hanamoto et al. | 436/161 |
| 4,507,390 | 3/1985 | Hotiuchi et al. | 436/67 |
| 4,661,728 | 4/1987 | Wagner | 436/67 |
| 4,767,529 | 8/1988 | Boos et al. | 210/198.2 |
| 4,802,981 | 2/1989 | Kenney et al. | 422/70 |
| 5,137,833 | 8/1992 | Russel | 436/131 |

OTHER PUBLICATIONS

Reid, et al.; Applications for Group Specific Ligands in Fast, High Performance Affinity Chromatography; *Biochromatography*, vol. 3, No. 5 (1988).

Middle et al.; Separation of glycosylated hemoglobins using immobilized phenylboronic acid; *Biochem. J.*, 209:771–779 (1985).

Gould et al.; Measurement of glycosylated hemoglobins using an affinity chromatography method; *Clinica Chimica Acta*; 125:41–48 (1982).

Fluckiger, et al.; Quantitation of glycosylated hemoglobin by boronate affinity chromatography; *Diabetes*, 33:73–76 (1984).

Mallia et al.; Preparation and use of a boronic acid affinity support for separation and quantitation of glycosylated hemoglobins; *Analytical Letters*; 14(B8):649–661 (1981).

Dean et al.; Applications of Immobilised Boronic Acids; *Affinity Chromatography and Biological Recognition*; 433–443 (1983).

Bannon et al.; Glycated hemoglobin in uremic patients as measured by affinity and ion–exchange chromatography; *Clinical Chemistry*; 30(3):485–486 (1984).

Little et al.; Glycosylated hemoglobin measured by affinity chromatography: Microsample collection and room–temperature storage; *Clin. Chem.*, 29(6):1080–1082 (1983).

Willey et al.; Glycosylated haemoglobin and plasma glycoprotein assays by affinity chromatography; *Diabetologia*, 27:56–58 (1984).

Papedea et al.; The effect of storage conditionson ion exchange and affinity chromatographic assays for glycated hemoglobin; *Clinical Biochemistry*, 17:296–301 (1984).

Talwar et al.; Determination of glycosylated adult and foetal haemoglobins by affinity chromatography; *Clinica Chimica Acta.*, 128:61–67 (1983).

John et al.; Affinity chromatography method for the measurement of glycosylated haemoglobin: comparison with two methods in routine use; *Clinica Chimica Acta.*, 136:257–262 (1984).

Klenk et al.; Determination of glycosylated hemoglobin by affinity chromatography: comparison with colorimetric and ion–exchange methods, and effects of common interferences; *Clin. Chem.*, 28(10) (1982).

Little et al.; Effects of whole blood storage on results for glycosylated hemoglobin as measured by ion–exchange chromatography, affinity chromatography and colorimetry; *Clin. Chem.*, 29(6):1113–1115 (1983).

Peterson et al.; A comparative evaluation of glycosylated haemoglobin assays: feasibility of references and standards; *Diabetologia*, 26:214–217 (1984).

Herold et al.; Measurement of glycosylated hemoglobins using boronate affinity chromatography; *Ann. Clin. & Lab. Sci.*, 13(6):482–488 (1983).

Gould et al.; A sensitive method for the measurement of glycosylated plasma proteins using affinity chromatography; *Am. Clin. Biochem.*, 21:16–21 (1984).

Mullins et al.; Sensitivity of isoelectric focusing, ion exchange and affinity chromatography to labile glycated hemoglobin; *Clin. Chem.*, 32(8):1460–1463 (1986.

Dean; Measurement of glycosylated haemoglobins using affinity chromatography; *Diabetologia*, 21:579–580 (1981).

Hall et al.; Measurement of glycosylated haemoglobins and glycosylated plasma proteins in maternal and cord blood using an affinity chromatography method; *Diabetologia*, 25:477–481 (1983).

Bruns et al.; Specific affinity–chromatographic measurement of glycated hemoglobins in uremic patients; *Clin. Chem.*, 30(4):569–571 (1984).

Abraham et al.; application of affinity chromatography for separation and quantitation of glycosylated hemoglobins; *J. Lab. Clin. Med.*, 187–197 (1983).

Fairbanks et al.; Measurement of glycosylated hemoglobin by affinity chromatography; *Mayo Clin. Proc.*, 58:770–773 (1983).

McLennan et al.; The measurement of glycosylated hemoglobin in man and animals by aminophenylboronic acid affinity chromatography; *Diabetes*, 31:701–705 (1982).

Hall et al.; Glycosylated hemoglobins and glycosylated plasma proteins in the diagnosis of diabetes mellitus and impaired glucose tolerance; *Diabetes Care*, 7(2):147–150 (1984).

Fluckiger et al.; Measurement of nonenzymatic protein glycosylation; *Methods in Enzymology*, 106:77–87 (1984).

Yatscoff et al.; Evaluation of an affinity chromatographic procedure for the determination of glycosylated hemoglobin (HbA1); source unknown; pp. 291–295.

Garlick et al.; Characterization of glycosylated hemoglobins; *J. Clin. Invest.*, 71:1062–1072 (1983) Glycosylated Albumin; Endocrine Sciences.

Ou et al.; Rapid Analysis of Hemoglobin Variants by Cation–Exchange HPLC; Clin. Chem.; 39/5, 820–824 (1993).

Turpeinen et al.; Two α–Chain Hemoglobin Variants, Hb Broussais and Hb Bemenelum, Characterized by Cation–Exchange HPLC, Isoelectric Focusing and Peptide Sequencing; Clin. Chem. 41/4, 532–536 (1995).

Huisman, Separation of Hemoglobins and Hemoglobin Chains by High–Performance Liquid Chromatography; J. Chromatog. 418 (1987) 277–304.

Turpeinen; Liquid Chromatographic Determination of Hemoglobin $A_2$; Clin. Chem. 32/6, 999–1002 (1986).

Huisman, et al.; Microchromatography of hemoglobins. III. A simplified procedure for the determination of hemoglobin $A_2$; J. Lab. Clin. Med. (1975); vol. 86, No. 4, pp. 700–703.

Bisse et al.; High–Performance Liquid Chromatographic Separation of Human Haemoglobins; J. Chromatog. 434 (1988) 95–110.

Roger s et al.; High–Performance Liquid Chromatography in the Diagnosis of Hemoglobinopathies and Thalassemias; A.J.C.P. (1985), vol. 84, No. 5, pp. 671–674.

Pembrey et al.; Reliale routine estimate of small amounts of foetal haemoglobin by alkali denaturation; J. Clin. Path., vol. 25 (1972) 738–740.

Wessels et al.; Liquid Chromatography Used in Diagnosis of a Rare Hemoglobin Combination: Hemoglobin S/Lepore; Clin. Chem. 32/5, 903–906 (1986).

Wilson et al.; A New High–Performance Liquid Chromatographic Procedure for the Separation and Quantitation of Various Hemoglobin Variants in Adults and Newborn Babies; Wilson et al.; J. Lab. Clin. Med. 102: 174, 1983.

Ou et al.; High–Performance Liquid Chromatography of Human Hemoglobins on a New Cation Exchanger; J. Chromatog. 266 (1983) 197–205.

Roa et al.; Reference Ranges for Hemoglobin Variants by HPLC in African Americans; Ann. Clin & Lab. Sci., vol. 25, No. 3 (1995 228–235.

Abstract No. 222: A cation–exchange high performance liquid chromatographic assay for hemoglobin A1c and hemoglobin screening; Clin. Chem., vol. 31, No. 6, (1985).

*Primary Examiner*—James Ketter
*Attorney, Agent, or Firm*—Hovey, Williams, Timmons & Collins

[57] ABSTRACT

Improved HPLC methods for the identification and characterization of hemoglobin variants in blood samples are disclosed. These methods are performed manually or with the aid of a computer. In preferred embodiments, a blood sample is injected into an HPLC unit and hemoglobin species from the blood sample are separated using high column temperatures and high eluant flow rates. Blood samples are initially screened using a low-resolution HPLC method to determine if an eluted hemoglobin species has a characteristic indicative of a hemoglobin variant, i.e., if a chromatograph peak of the eluted species has one of a number of parameter values falling within a predetermined range of values. If the initial screening indicates that a blood sample may have a hemoglobin variant, the blood sample is subsequently reanalyzed using a high-resolution HPLC method to determine if an eluted hemoglobin species corresponds to a known hemoglobin variant by comparing the retention time of an eluted species to the retention times of known hemoglobin variants. Alternatively, both the low-resolution and high-resolution HPLC methods can be used independently of one another. Thus, the methods of the invention are useful in putatively identifying abnormal hemoglobins.

35 Claims, 8 Drawing Sheets

| NUM | RT | REL RT | | Width | Area % | Comment |
|---|---|---|---|---|---|---|
| 1 | .187 | RT F | .301 | .045 | 1.2 | 3 |
| 2 | .250 | RT F | .402 | .060 | 1.6 | |
| 3 | .445 | RT F | .715 | .128 | 3.3 | $A_{1c}$ Peak |
| 4 | .787 | RT F | 1.265 | .058 | 1.8 | |
| 5 | .855 | RT A | .858 | .050 | 1.9 | |
| 6 | .986 | RT A | .989 | .040 | 53.5 | $A_o$ Peak 2 |
| 7 | 1.099 | RT A | 1.102 | .065 | 5.6 | $A_2$ Peak 3 3 |
| 8 | 1.262 | RT S | .986 | .049 | 31.1 | 3 3 |

FIG. 3.

| Sample Number | Peak Number | RT | REL RT | Width | Area % | Code |
|---|---|---|---|---|---|---|
| 2 | 1 | .340 | .584 | .164 | 24.9 | 3 |
| 2 | 2 | .609 | 1.046 | .124 | 22.5 | 3 |
| 2 | 3 | .807 | .804 | .114 | 10.1 | 3 |
| 2 | 4 | .996 | .992 | .052 | 42.5 | 2 |
| 3 | 1 | .255 | .438 | .117 | 6.3 | 3 |
| 3 | 3 | .875 | .872 | .117 | 6.7 | 3 |
| 3 | 4 | 1.000 | .996 | .055 | 72.5 | 2 |
| 3 | 5 | 1.107 | 1.103 | .069 | 10.0 | 3 3 |
| 4 | 2 | .930 | .926 | .079 | 6.7 | 3 |
| 4 | 3 | 1.085 | 1.081 | .069 | 30.5 | 3 |
| 4 | 4 | 1.299 | 1.025 | .091 | 4.9 | 3 |
| 4 | 5 | 1.492 | 1.178 | .079 | 7.7 | 3 3 |
| 4 | 6 | 1.755 | 1.010 | .137 | 47.3 | 3 3 |
| 12 | 1 | .205 | .352 | .109 | 9.8 | 3 |
| 12 | 2 | .441 | .758 | .107 | 32.2 | 3 |
| 12 | 5 | 1.000 | 1.001 | .052 | 53.8 | 2 |
| 13 | 1 | .250 | .430 | .138 | 8.3 | 3 |

| NUM | RT | REL RT | | Width | Area % | Comment |
|---|---|---|---|---|---|---|
| 1 | .219 | RT F | .106 | .077 | 1.4 | |
| 2 | .446 | RT F | .215 | .097 | 1.2 | |
| 3 | 1.581 | RT F | .763 | .174 | 3.9 | $A_{1c}$ Peak |
| 4 | 1.901 | RT F | .917 | .232 | 3.9 | F Peak |
| 5 | 2.975 | RT F | 1.436 | .194 | 1.7 | |
| 6 | 4.004 | RT A | 1.009 | .169 | 58.9 | $A_o$ Peak |
| 7 | 4.821 | RT A | 1.215 | .168 | 2.8 | $A_2$ Peak |
| 8 | 5.698 | RT S | 1.000 | .208 | 26.2 | |

FIG.5.

| VARIANT | RANGE |
|---|---|
| Barts | .093-.128 |
| Acetyl F | .323-.459 |
| H | .471-.495 |
| Acetyl S. Florida | .638-.706 |
| $A_{1c}$ | .718-.880 |
| Hope | .855-.901 |
| F | .900-1.054 |
| Camden | .901-1.018 |
| I | .989-1.088 |
| N. Baltimore | 1.164-1.240 |
| I. High Wycombe | 1.326-1.414 |
| J. Baltimore | 1.385-1.461 |
| Fannin Lubbock | 1.459-1.524 |

FIG. 6.

| VARIANT | RANGE |
|---|---|
| I. High Wycombe | .688- .760 |
| J. Baltimore | .719- .802 |
| Fannin Lubbock | .758- .819 |
| S. Florida (peak 1) | .921- .967 |
| A | .976-1.035 |
| Westmead | .992-1.008* |
| S. Florida (peak 2) | .993-1.005* |
| Chicago | 1.001-1.010* |
| Lepore Baltimore | 1.001-1.058* |
| Lepore Boston | 1.050-1.144 |
| P. Galveston | 1.065-1.080 |
| G. Couchatta | 1.082-1.138 |
| Zurich | 1.151-1.162 |
| E | 1.150-1.193 |
| $A_2$ | 1.180-1.247 |
| Osu Christianborg | 1.195-1.208 |
| Korle Bu | 1.206-1.254 |
| Koln (peak 1) | 1.230-1.303 |
| G. Philadelphia | 1.237-1.298 |
| D. Punjab | 1.262-1.328 |

*Heterozygous forms with A are the only forms known; these variants are not separated from A well enough to give two peaks; however, they are easily recognized as variants since the combination of A and variant migrates as a single peak with a retention time slightly different than the retention time of A alone; the combined A and variant peaks are also significantly broader than the A peak alone.

FIG. 7.

| VARIANT | RANGE |
|---|---|
| G. Couchatta | .760- .799 |
| E | .819- .843 |
| $A_2$ | .828- .886 |
| Osu Christianborg | .826- .868 |
| Koln (Peak 1) | .850- .895 |
| Korle Bu | .863- .880 |
| G. Philadelphia | .890- .904 |
| Russ | .914- .938 |
| D | .913- .931 |
| D.Punjab | .920- .954 |
| E. Saskatoon | .921- .945 |
| Deer Lodge | .956-1.008 |
| S | .988-1.031 |
| Q. Thailand | 1.001-1.021 |
| Montgomery | 1.010-1.036 |
| $A_2'$ | 1.038-1.066 |
| Koln (peak 2) | 1.051-1.085 |
| Q. India | 1.058-1.084 |
| G. San Jose | 1.066-1.092 |
| Sealy (Hasharon) | 1.078-1.108 |

FIG. 8.

| VARIANT | RANGE |
|---|---|
| O.Arab | .914 - .929 |
| C | .922 - 1.018 |

| NUM | RT | REL RT | | Width | Area % | Comment |
|---|---|---|---|---|---|---|
| 1 | .300 | RT F | .158 | .092 | 1.4 | |
| 2 | .424 | RT F | .223 | .151 | 3.0 | |
| 3 | 1.385 | RT F | .728 | .199 | 3.1 | |
| 4 | 1.581 | RT F | .831 | .327 | 7.1 | |
| 5 | 2.281 | RT F | 1.199 | .277 | 3.4 | |
| 6 | 3.179 | RT A | .840 | .274 | 2.3 | |
| 7 | 3.802 | RT A | 1.004 | .195 | 74.8 | |
| 8 | 4.650 | RT A | 1.229 | .172 | 4.8 | $A_2$ Peak |

F = 0%    $A_2$ = 4.8%

| Sample | %F | % $A_2$ |
|---|---|---|
| 1 | .0 | 2.2 |
| 2 | .0 | 2.0 |
| 3 | .0 | 4.0 |
| 4 | .0 | VARIANT PRESENT - INVALID RESULT |
| 5 | 68.3 | .0 |
| 6 | 62.4 | .0 |

CHROMATOGRAPHIC METHOD FOR THE IDENTIFICATION AND CHARACTERIZATION OF HEMOGLOBIN VARIANTS IN BLOOD

MICROFICHE APPENDIX

A microfiche appendix containing the source code of a computer program useful in the present invention is appended hereto as one sheet of microfiche containing 42 frames.

BACKGROUND OF THE INVENTION

1. Field of the Invention

The present invention is broadly concerned with improved HPLC methods useful in identifying and characterizing hemoglobin variants in blood. More particularly, the present invention relates to methods in which a blood sample is injected into an HPLC unit and hemoglobin species from the blood sample are separated using high column temperatures and high eluant flow rates; chromatographic data regarding the separated hemoglobin species are analyzed manually or with the aid of a computer to determine if an eluted hemoglobin species has a characteristic indicative of a hemoglobin variant, and/or to determine if an eluted hemoglobin species corresponds to a known hemoglobin variant; hemoglobin abnormalities are thereby putatively identified.

2. Description of the Prior Art

The hemoglobin molecule is composed of a prosthetic heme group attached to two pairs of unlike polypeptide chains. Normal adult hemoglobin (A) consists of two $\alpha$ and two $\beta$ chains ($\alpha_2\beta_2$). A second normal adult hemoglobin ($A_2$) consists of two $\alpha$ and two $\delta$ chains ($\alpha_2\delta_2$). The primary structure of the $\delta$ chain differs from that of the $\beta$ chain at ten amino acid positions. The blood of normal adult humans contains both A as the major hemoglobin species and $A_2$ as a minor hemoglobin species. Human fetuses and newborn infants produce mainly fetal hemoglobin (F) which consists of two $\alpha$ chains and two $\gamma$ chains. The $\beta$ and $\gamma$ chains differ at 39 amino acid positions. Additionally, the $\delta$ chain and the $\epsilon$ chain have been observed in early human embryos. Newborn infants have two types of $\gamma$ chain, the $^G\gamma$ chain which has a glycine residue at position 136, and the $^A\gamma$ chain which has an alanine residue at position 136. Thus, seven types of hemoglobin chains exist in the human, namely $\alpha$, $\gamma$, $^A\gamma$, $^G\gamma$, $\delta$, and $\epsilon$ chains.

The first abnormal hemoglobin discovered (S) is responsible for sickle cell anemia. S is the result of a substitution of a valine residue for the glutamate residue normally found at position 6 of the $\beta$ chain. Another relatively common abnormal hemoglobin is C. Most of the hundreds of hemoglobin variants, discovered over the last 40 to 50 years, are the result of single base substitutions in the DNA of either the $\alpha$, $\beta$, $^A\gamma$, $^G\gamma$, or $\delta$ globin genes, but other variants with hybrid chains, extended chains, and chains with deletions have been discovered. The detection of abnormal hemoglobin variants is the primary method of diagnosing hemoglobinopathies.

Approximately 90% of total hemoglobin is nonglycosylated. The major fraction of nonglycosylated hemoglobin is nonglycosylated A, referred to as $A_0$. The major fraction of glycosylated hemoglobin is glycosylated A, referred to as $A_{1c}$. $A_{1c}$ arises by reaction of a terminal valine amine group in the $\beta$ chain with the aldehyde group of glucose to give an unstable aldimine. Amadori rearrangement of the aldimine gives $A_{1c}$, which is characterized by a $\beta$-ketoglycoside linked to the valine amine group. The determination of the concentration of $A_{1c}$ is useful in diagnosing diabetes mellitus and in monitoring the treatment of the disease. In nondiabetic individuals, the $A_{1c}$ level is generally between 4 to 8% of total hemoglobin. In diabetics, the $A_{1c}$ level is two- to three-fold higher and may range up to 20% of total hemoglobin.

Numerous procedures have been used to identify and characterize normal and abnormal hemoglobins. Traditionally, these methods have included electrophoresis, isoelectric focusing, and macro-chromatography. During the past several years, high-performance liquid chromatography (HPLC) has been applied to the study of hemoglobinopathies and diabetes mellitus. Advantages of HPLC include relatively high sensitivity, specificity, and speed of analysis. However, HPLC methods generally lack the resolution necessary to differentiate some commonly encountered hemoglobin variants, and also lack the sensitivity required to detect hemoglobins at low concentrations. Additionally, most HPLC methods do not offer computer-assisted analysis of the resultant data, and therefore require time-consuming manual analysis.

A high-resolution cation-exchange HPLC method using a polyaspartic acid-containing column was described by Ou and Rognerud in Clin. Chem. 39(5): 820–824(1993), the teachings of which are incorporated by reference herein. Although this method was capable of resolving more than 35 commonly encountered hemoglobin variants, at least 20 minutes were required for each sample run. Furthermore, this method was not coupled with an automated system of data analysis.

SUMMARY OF THE INVENTION

The present invention is directed to improved HPLC methods useful in putatively identifying and characterizing hemoglobin variants in blood. These methods include the steps of injecting a blood sample into the column of an HPLC unit, separating different hemoglobin species from the blood sample, and individually analyzing the different hemoglobin species. These methods overcome problems encountered in the prior art in that blood samples are analyzed at high speeds. These high speeds are made possible by maintaining the HPLC column at a temperature greater than 25° C. (preferably from about 30° C. to 50° C.), and/or by using an eluant flow rate of greater than 1.5 ml/minute (preferably from about 2 ml/minute to 3.5 ml/minute). Moreover, the analysis of chromatographic data may be conducted with the aid of a computer to further increase the speed with which abnormal hemoglobins may be identified.

In preferred embodiments, a blood sample is analyzed in a two-step process. In the first step, the blood sample is analyzed by passing a first aliquot of the sample through an HPLC unit at a relatively low first resolution. Hemoglobin species are eluted from the column, and are characterized as a function of their respective absorbance values and retention times (i.e., relative retention times and/or absolute retention times). An eluted species has a characteristic indicative of a hemoglobin variant if a chromatograph peak of the eluted species has a parameter value falling within a predetermined range of values, e.g., if a peak (a) is not an $A_0$ or $A_{1c}$ peak and has an area percent value greater than 5%, (b) appears in the $A_{1c}$ window and has an area percent value greater than 10%, (c) appears in the $A_0$ window and has an area percent value less than 80%, (d) appears in the $A_0$ window and has a width greater than 1.2 times the width of the marker $A_0$ peak, (e) appears in the degradation products window and has an area percent value greater than 10%, (f) appears after the $A_2$ window, (g) appears in the hemoglobin Bart's window and has an area percent value greater than 1%, or (h) appears in the $A_2$ window and has an area percent value greater than 10%.

If a species eluted in the first step has a characteristic indicative of a hemoglobin variant, the blood sample is further analyzed in a second step by passing a second aliquot of the blood sample through an HPLC unit at a relatively high second resolution. Again, hemoglobin species are eluted from the column, and are characterized as a function of their respective absorbance values and retention times (i.e., relative retention times and/or absolute retention times). A characteristic of an eluted species is then compared to characteristics of known hemoglobin variants to determine if the eluted species corresponds to a known hemoglobin variant (e.g., the relative retention time of an eluted species is compared to relative retention times of known hemoglobin variants). Hemoglobin variants include genetic variants such as Barts, Acetyl F, H, Acetyl S, Florida, Hope, F, Camden, L, N, Baltimore, I, High Wycombe, J. Baltimore, Fannin Lubbock, S. Florida (peak 1), Westmead, S. Florida (peak 2), Chicago, Lepore Baltimore, Lepore Boston, P. Galveston, G. Couchatta, Zurich, E., Osu Christianborg, Korle Bu, Koln (peak 1), G. Philadelphia, D. Punjab, Russ. D., E. Saskatoon, Deer Lodge, S., Q. Thailand, Montgomery, $A_2'$, Koln (peak 2), Q. India, G. San Jose, or Sealy (Hasharon).

Advantageously, the two-step process described above is used to sequentially analyze a plurality of blood samples. Preferably, the injection-to-injection time in the low-resolution and high-resolution methods is less than 20 minutes (ideally from about 2 to 4 minutes in the low-resolution method and from about 8 to 12 minutes in the high-resolution method). Alternatively, both the low-resolution and high-resolution methods can be used independently of one another to analyze a plurality of blood samples as described above.

BRIEF DESCRIPTION OF THE DRAWINGS

FIG. 3 shows an example of a batch summary report generated using the Quick Scan method to analyze patients' blood, wherein "RT" refers to absolute retention time and "REL RT" refers to relative retention time;

FIG. 5 shows a table giving the expected ranges of relative retention times for hemoglobin variants migrating the closest to hemoglobin F;

FIG. 6 shows a table giving the expected ranges of relative retention times for hemoglobin variants migrating the closest to hemoglobin A;

FIG. 7 shows a table giving the expected ranges of relative retention times for hemoglobin variants migrating the closest to hemoglobin S;

FIG. 8 shows a table giving the expected ranges of relative retention times for hemoglobin variants migrating the closest to hemoglobin C;

DETAILED DESCRIPTION OF THE PREFERRED EMBODIMENT

Figure 1:
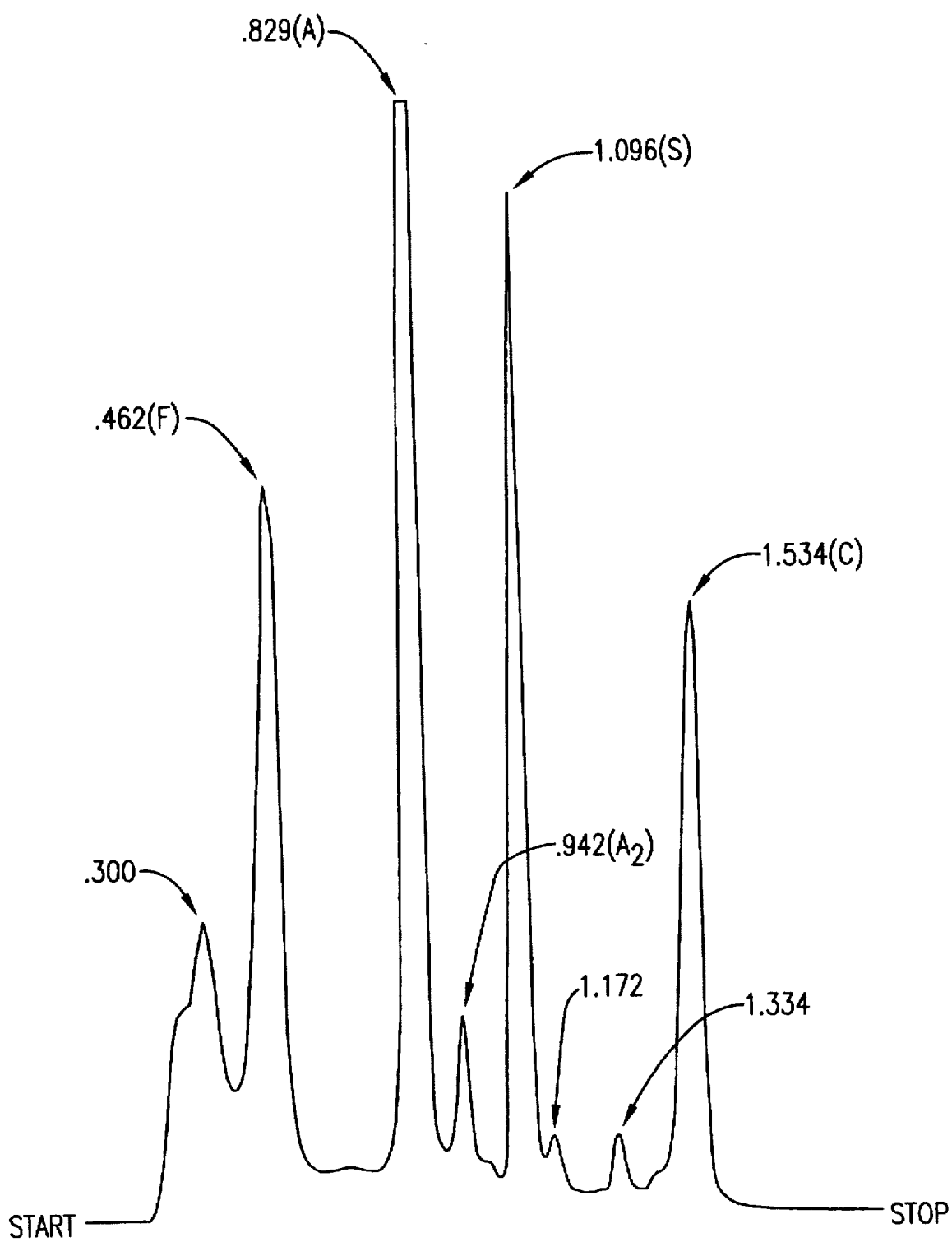
FIG. 1 is a Quick Scan chromatograph of a hemoglobin control showing absolute retention times for the F, A, S, C, and $A_2$ peaks.

The present invention is directed to a chromatographic method for the identification and characterization of hemoglobin variants in blood samples from patients. This invention includes the following methods: Startup, Standby, Quick Scan, High Resolution, Quick Scan/High Resolution, $A_2$ and F Quantitation, and Shutdown.

After the HPLC unit is turned on, the Startup method is used to prepare the unit for sample analysis. The Standby method is then selected in order to maintain the HPLC unit in a ready condition without wasting reagents. A batch run is subsequently conducted, i.e., a number of samples are analyzed using the Quick Scan method and/or the High Resolution method, or the $A_2$ and F Quantitation method. When the Quick Scan/High Resolution method is used, aliquots of all samples are analyzed using the Quick Scan method. If an abnormal hemoglobin is thereby detected in a sample, a second aliquot of that sample is reanalyzed using the High Resolution method.

If more than one batch run is being conducted, the Standby method is selected after each batch run in order to maintain a ready condition between batch runs. Also, the Standby method is selected between the Quick Scan phase and High Resolution phase of the Quick Scan/High Resolution method. The Shutdown method is selected after the final batch run is completed; in this method, the column is washed, and the HPLC unit is turned off.

The preferred embodiments of the present invention are illustrated in the example below. However, nothing therein shall be taken as a limitation upon the overall scope of the invention.

EXAMPLE

Instrumentation.

The HPLC unit used in the chromatographic analysis of hemoglobin was the continuous, automated Hewlett Packard 1090 as modified by Primus Corporation and known as the Primus CLC330. This unit included a proportioning valve, a metering pump, a high pressure booster pump, an auto sampler, an auto injector, a photometric detector, dual disc drives, a recording integrator, a temperature-controlled oven, and an HP LUCI controller. However, the analysis can be conducted with any high-quality HPLC system using the appropriate parameters.

Chemistry.

Separation of hemoglobin components took place on a cation exchange column. Specifically, a polyaspartic acid column (3.5 cm×0.46 cm) including a porous silica support having a 5 um particle size and a pore size of 100 nm was used, although many other types of cation exchange columns can be employed. Two mobile phases were used in the HPLC unit. Mobile phase 1 was composed of 10 mM Bis-Tris and 1 mM KCN, and had a pH of 7.0. Mobile phase 2 was composed of 10 mM Bis-Tris, 1 mM KCN, and 200 mM NaCl, and had a pH of 6.6. The amounts of mobile phase 1 and mobile phase 2 in a mixture thereof are represented below as volume percentages relative to the total volume of the mixture. The test samples contained whole blood hemolysate prepared by dilution of one part whole blood with from about 20 to 500 parts purified water (preferably from about 50 to 200 parts purified water, and ideally 100 parts purified water). Sodium azide (0.001%) was added as a preservative. The injection volume was from about 1 ul to 25 ul (preferably from about 2.5 ul to about 10 ul, and ideally 5 ul) of the diluted (i.e., hemolyzed) sample.

Startup Method.

When the Startup method was selected, the lamp and pumps were turned on. The flow rate of eluant was set to 2.5 ml/minute, and the column temperature was set to 40° C. Initially, 100% mobile phase 2 was pumped through the system for 4.9 minutes (i.e., from time 0 to time 4.9 minutes). From time 4.9 minutes to time 5.0 minutes, the composition of the eluant was changed in a linear fashion from 100% mobile phase 2 to 90% mobile phase 1 and 10% mobile phase 2; this condition was held constant from time 5.0 minutes to time 10.0 minutes. From time 10.0 minutes to time 13.0 minutes, the composition of the eluant was changed in a linear fashion from 90% mobile phase 1 and 10% mobile phase 2 to 60% mobile phase 1 and 40% mobile phase 2. From time 13.0 minutes to time 16.0 minutes, the composition of the eluant was changed in a linear fashion from 60% mobile phase 1 and 40% mobile phase 2 to 100% mobile phase 2. At time 16.0, the Standby method was selected.

Standby Method.

When the Standby method was selected, the flow rate was reduced to 0.15 ml/minute, the mobile phase composition was kept constant at 90% mobile phase 1 and 10% mobile phase 2, the lamp was kept on, and the column oven temperature was maintained at 40° C.

Quick Scan Method.

When the Quick Scan method was used, the column was equilibrated over 1.5 minutes with a mixture of 85% mobile phase 1 and 15% mobile phase 2 at a constant flow rate of 3 ml/minute. Throughout the analysis (i.e., during equilibration and thereafter), the column temperature was maintained at 40° C., and the eluant employed was passed through the column at a flow rate of 3 ml/minute. A non-linear mobile-phase gradient covering a range of concentrations from 85% mobile phase 1 and 15% mobile phase 2 to 20% mobile phase 1 and 80% mobile phase 2 was used to separate hemoglobin components. The gradient changes took place over 1.2 minutes. Thereafter, the conditions were returned to the starting conditions over 0.3 minute.

The non-linear mobile phase gradient included the following steps. At time of injection (i.e., time zero), the eluant consisted of 85% mobile phase 1 and 15% mobile phase 2. Over the first minute (i.e., to time 1.0 minute), the composition of the eluant was changed in a linear fashion to consist of 35% mobile phase 1 and 65% mobile phase 2. From time 1.0 minute until time 1.2 minutes, the eluant was changed in a linear fashion to consist of 20% mobile phase 1 and 80% mobile phase 2. From time 1.2 minutes to time 1.5 minutes, the eluant was changed in a linear fashion back to the original composition (i.e., 85% mobile phase 1 and 15% mobile phase 2). This eluant condition was then maintained for an additional 1.5 minutes (i.e., until time 3.0 minutes). Thus, a total time of 3.0 minutes elapsed from injection to injection.

The first sample of a batch run was a known marker sample containing F, A, $A_2$, S, and C. However, any other hemoglobin sample could also be used in lieu of the marker sample. Results of this first injection were ignored. The second sample injected was the marker sample. The sequential order of elution of the hemoglobin species in the marker sample is known to be F, A, $A_2$, S, and C (the largest peak between the A and S peaks is known to be the $A_2$ peak). The resultant chromatograph, an example of which is shown in FIG. 1, was used to calculate the absolute retention time, area percent value, and peak width for each of F, A, $A_2$, S, and C. Area percent value refers to the percentage of a particular species' integrated peak area relative to the total integrated peak area of the entire chromatograph. When using the Quick Scan method, High Resolution method, Quick Scan/High Resolution method, or $A_2$ and F Quantitation method, marker samples were used as described above to recalibrate the HPLC unit with respect to absolute retention times, area percent values, and peak width usually after 20 unknown sample runs. However, recalibration was necessary only after 100 sample runs.

The rules shown in Table 1 were used to identify abnormal hemoglobin species in blood samples.

TABLE 1

Rules used to identify abnormal hemoglobin patterns in Quick Scan chromatographs.

| Rule | Description |
|---|---|
| 1 | Any peak (other than the $A_0$ or $A_{1c}$ peaks) having an area percent value greater than 5% is flagged (code 3).[1] |
| 2 | Any peak in the $A_{1c}$ window having an area percent value greater than 10% is flagged (code 3).[2, 3] |
| 3 | Any peak in the $A_0$ window having an area percent value less than 80% is flagged (code 2).[4] |
| 4 | Any peak in the $A_0$ window having a width greater than 1.2 times the width of the marker $A_0$ peak is flagged (code 1).[5] |
| 5 | Any peak in the degradation products window having an area percent value greater than 10% is flagged (code 3).[6] |
| 6 | Any peak eluting after the $A_2$ window is flagged (code 3). |
| 7 | Any peak in the hemoglobin Bart's window having an area percent value greater than 1% is flagged (code 3). |
| 8 | If any peak in the $A_2$ window has an area percent value greater than 10%, the result is printed as not valid for $A_2$ quantitation and thus signals the presence of a variant comigrating with $A_2$ |

[1] See Table 2 for Quick Scan codes.
[2] See Table 3 for windows for $A_{1c}$, $A_0$, degradation products, $A_2$, and hemoglobin Bart's.
[3] The $A_{1c}$ peak has an area percent value greater than 10% of total hemoglobin only when an abnormal hemoglobin is present or in poorly controlled diabetes.
[4] The $A_0$ peak has an area percent value always greater than 80% of total hemoglobin except in cases of thalassemia, abnormal hemoglobin, or in very poorly controlled diabetes.
[5] When $A_0$ and hemoglobin variants eluting very close to $A_0$ were both present in the same sample, the two hemoglobins blended together as a single peak which was shorter and broader than a peak composed of a single substance.
[6] Degradation products result from hemoglobin degradation in older samples.

TABLE 2

Quick Scan codes.

| Code | Description |
|---|---|
| 1 | The width of the $A_0$ peak is greater than 1.2 times the width of the marker $A_0$ peak. |
| 2 | The area percent value of the $A_0$ peak is less than 80%. |

TABLE 2-continued

Quick Scan codes.

| Code | Description |
|---|---|
| 3 | The area percent value of any peak other than the $A_0$ peak is greater than the expected area percent value for that peak. |

TABLE 3

Quick Scan windows for $A_{1c}$, $A_0$, degradation products, $A_2$, hemoglobin Bart's, and F.

| Hemoglobin | Window[1] |
|---|---|
| $A_{1c}$ | 0.62–0.89[2] |
| $A_0$ | 0.98–1.03[3] |
| Degradation Products | 0.72–0.89[4] |
| $A_2$ | 1.05–1.20[5] |
| Bart's | <0.189[6] |
| F | 0.90–1.05[7] |

[1]Windows are expressed either as a range of values for either absolute retention time or relative retention time; relative retention time is determined by dividing the absolute retention time of one species by the absolute retention time of another species; the window for each particular species noted in Table 3 was determined experimentally by running one or more samples known to contain that species.
[2]Relative retention time (absolute retention time of known $A_{1c}$ divided by the absolute retention time of marker F).
[3]Relative retention time (absolute retention time of known $A_0$ divided by the absolute retention time of marker A).
[4]Relative retention time (absolute retention time of known degradation products divided by the absolute retention time of marker A).
[5]Relative retention time (absolute retention time of known $A_2$ divided by the absolute retention time of marker A).
[6]Absolute retention time in minutes.
[7]Relative retention time (absolute retention time of known F divided by the absolute retention time of marker F, with known F and marker F being in different samples).

Figure 2:
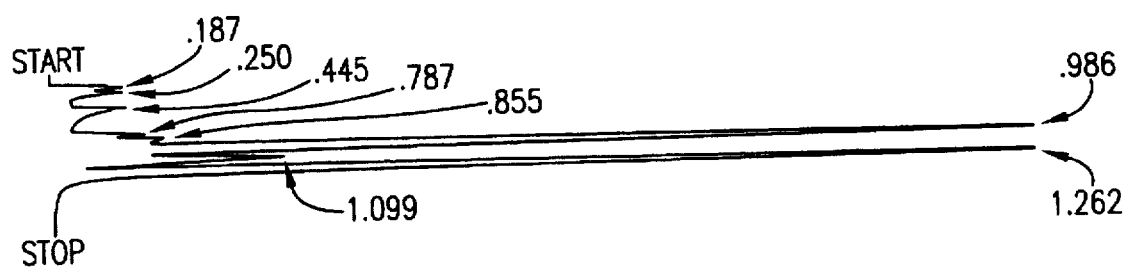
FIG. 2 shows an example of an individual sample report generated using the Quick Scan method to analyze a patient' blood, wherein "NUM" refers to blood sample number, "RT" refers to absolute retention time, and "EL RT" refers to relative retention time.

After each unknown sample from a patient was run using the Quick Scan method, an individual sample report, an example of which is shown in FIG. 2, was automatically printed. Each individual sample report consisted of a chromatograph of the sample and a table including the following information: a) the number of each peak, b) the absolute retention time of the species giving the peak, c) the closest marker peak (i.e., F, A, S, or C), d) the relative retention time of the species giving the peak (i.e., the absolute retention time of the species giving the peak divided by the absolute retention time of the closest marker species), e) the width of the peak, f) the area percent value of the peak, and g) comments. Code numbers were included in the comments section. Also, a peak was putatively identified in the comments section as an F, $A_0$, $A_{1c}$, or $A_2$ peak by determining which species had a relative retention time (relative to known F, A, F, and A, respectively) falling within the F, $A_0$, $A_{1c}$, or $A_2$ window (see Table 3).

At the conclusion of each batch run, a batch summary report, an example of which is shown in FIG. 3, was printed automatically. Each batch summary report listed every sample which had been flagged as abnormal. The batch sample report included the following information: a) the sample number, b) the number of the peak which was abnormal, c) the absolute retention time of the species giving the peak, d) the relative retention time of the species giving the peak (i.e., the absolute retention time of the species giving the peak divided by the absolute retention time of the closest marker species), e) the width of the peak, f) the area percent value of the peak, and g) one or more of the code numbers described above.

High Resolution Method.

When the High Resolution method was used, the column was equilibrated over 1.6 minutes, and the flow rate was maintained at 2.5 ml/minute throughout the analysis. The temperature in the column oven was maintained at 40° C. The mobile phase composition was 90% mobile phase 1 and 10% mobile phase 2.

Hemoglobin components were separated using a non-linear mobile-phase gradient covering a range of concentrations from 90% mobile phase 1 and 10% mobile phase 2 to 0% mobile phase 1 and 100% mobile phase 2. The gradient changes took place over 7.9 minutes. This condition was maintained over the next 0.4 minute. Subsequently, conditions were returned to starting conditions over the next 0.1 minute.

Specifically, from time zero to time 2.0 minutes, the composition of the eluant was changed in a linear fashion from 90% mobile phase 1 and 10% mobile phase 2 to 80% mobile phase 1 and 20% mobile phase 2. From time 2.0 minutes to time 2.5 minutes, the composition of the eluant was changed in a linear fashion to 70% mobile phase 1 and 30% mobile phase 2. From time 4.5 minutes to time 5.2 minutes, the composition of the eluant was changed in a linear fashion to 65% mobile phase 1 and 35% mobile phase 2. From time 5.2 minutes to time 7.7 minutes, the composition of the eluant was changed in a linear fashion to 29.2% mobile phase 1 and 70.8% mobile phase 2. From time 7.7 minutes to time 7.9 minutes, the composition of the eluant was changed in a linear fashion to 100% mobile phase 2. This eluant condition was then maintained for an additional 0.4 minute until time 8.3 minutes. Finally, from time 8.3 minutes to time 8.4 minutes, the eluant was changed in a linear fashion back to the original composition (i.e., 90% mobile phase 1 and 10% mobile phase 2).

Figure 4:
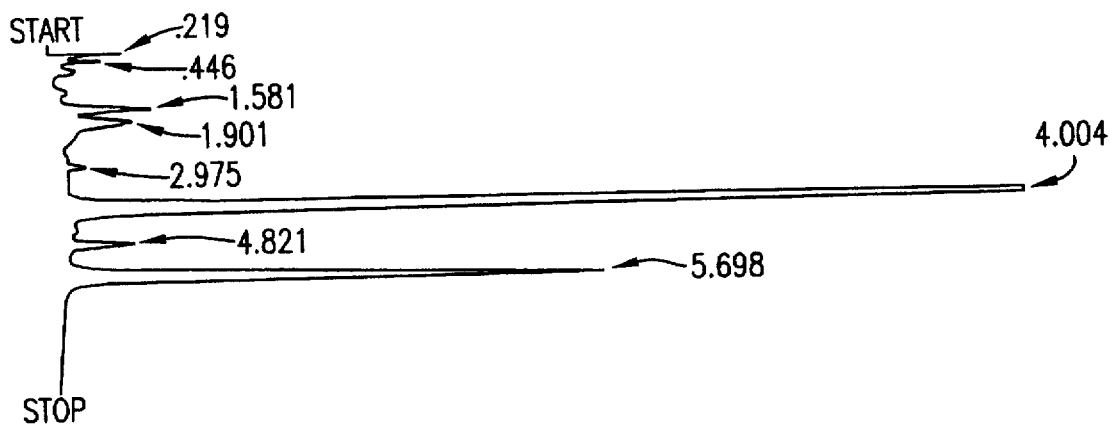
FIG. 4 shows an example of an individual report generated using the High Resolution method to analyze a patient's blood, wherein "NUM" refers to blood sample number, "RT" refers to absolute retention time, and "REL RT" refers to relative retention time.

The absolute retention times, area percent values, and peak width for each of F, A, $A_2$, S, and C were determined as in the Quick Scan method. An individual sample report was automatically printed after each unknown blood sample from a patient was run. This report, an example of which is shown in FIG. 4, listed the same information included in each Quick Scan individual sample report. As in the Quick Scan method, a peak was putatively identified as an F, $A_0$, $A_{1c}$, or $A_2$ peak by determining which species had a relative retention time (relative to known F, A, F, and A, respectively) falling within a F, $A_0$, $A_{1c}$, or $A_2$ window (see Table 4 for windows used in the High Resolution method). Additionally, if a peak in the $A_2$ window had an area percent value greater than 10%, the result was printed as not valid for $A_2$ quantitation and thus signaled the presence of a variant that comigrated with $A_2$. Batch summary reports were not generated after batch runs when the High Resolution method was used.

TABLE 4

High Resolution windows for $A_{1c}$, $A_0$, degradation products, $A_2$, hemoglobin Bart's, and F.

| Hemoglobin | Window[1] |
|---|---|
| $A_{1c}$ | 0.72–0.88[2] |
| $A_0$ | 0.98–1.03[3] |
| Degradation Products | 1.0–2.0[4] |
| $A_2$ | 1.18–1.28[5] |
| Bart's | <0.20[6] |
| F | 0.90–1.05[7] |

TABLE 4-continued

High Resolution windows for $A_{1c}$, $A_0$, degradation products, $A_2$, hemoglobin Bart's, and F.

| Hemoglobin | Window[1] |
| --- | --- |

[1]Windows are expressed either as a range of values for either absolute retention time or relative retention time; relative retention time is determined by dividing the absolute retention time of one species by the absolute retention time of another species; the window for each particular species noted in Table 4 was determined experimentally by running one or more samples known to contain that species.
[2]Relative retention time (absolute retention time of known $A_{1c}$ divided by the absolute retention time of known F).
[3]Relative retention time (absolute retention time of known $A_0$ divided by the absolute retention time of known A).
[4]Relative retention time (absolute retention time of known degradation products divided by the absolute retention time of known A).
[5]Relative retention time (absolute retention time of known $A_2$ divided by the absolute retention time of known A).
[6]Absolute retention time in minutes.
[7]Relative retention time (absolute retention time of known F divided by the absolute retention time of known F).

Subsequently, the relative retention time of each species identified in the comment section of the individual sample reports as F, $A_0$, $A_{1c}$, or $A_2$ was compared with ranges of relative retention times for a variety of variants. If the species was identified in the comment section as F, the relative retention time of this species (relative to marker F) was compared to the ranges of relative retention times given in the table shown in FIG. 5 either to putatively identify the species as a specific variant or to at least narrow down the range of possibilities to a few variants. For example, the species identified as F in the individual sample report shown in FIG. 4 has a relative retention time of 0.917.This value falls within the ranges of relative retention times for both F and the Camden variant. More precise data regarding the identification of the species can be obtained by running known F and known Camden variant side by side with the unknown species for direct comparison.

If the species was identified in the comment section as $A_{1c}$, the relative retention time of this species (relative to marker F) was also compared to the ranges of relative retention times given in the table shown in FIG. 5. For example, the species identified as $A_0$ in the report shown in FIG. 4 has a relative retention time of 0.763. This value falls within the range of relative retention times for $A_{1c}$. Thus, the initial identification of this species as $A_{1c}$ was further supported by the table.

If the species was identified in the comment section as $A_0$, the relative retention time of this species (relative to marker A) was compared to the ranges of relative retention times given in the table shown in FIG. 6. For example, the species identified as $A_0$ in the report shown in FIG. 4 has a relative retention time of 1.009. This value falls within the range of relative retention times for A. Again, the initial identification of this species as $A_0$ was further supported by the table.

Likewise, If the species was identified in the comment section as $A_2$, the relative retention time of this species (relative to marker A) was compared to the ranges of relative retention times given in the table shown in FIG. 6. For example, the species identified as $A_2$ in the report shown in FIG. 4 has a relative retention time of 1.215. This value falls within the range of relative retention times for $A_2$. As with $A_0$ and $A_{1c}$, the initial identification of this species as $A_2$ was further supported by the table.

If a species migrating the closest to S was identified, the relative retention time of this species (relative to marker S) was compared to the ranges of relative retention times given in the table shown in FIG. 7. For example, the species represented by peak number 8 in the report shown in FIG. 4 has a relative retention time of 1.000. This value falls within the ranges of relative retention times for both S and the Deer Lodge variant. More precise data regarding the identification of the species can be obtained by running known S and known Deer Lodge variant side by side with the unknown species for direct comparison.

If a species migrating the closest to C is identified, the relative retention time of this species (relative to marker C) is compared to the ranges of relative retention times given in the table shown in FIG. 8. For example, a species represented by a peak in an individual summary report having a relative retention time of 0.920 is putatively identified as the O. Arab variant. More precise data regarding the identification of the species can be obtained by running O. Arab variant side by side with the unknown species for direct comparison.

$A_2$ and F Quantitation Method.

Figures 9, 10:
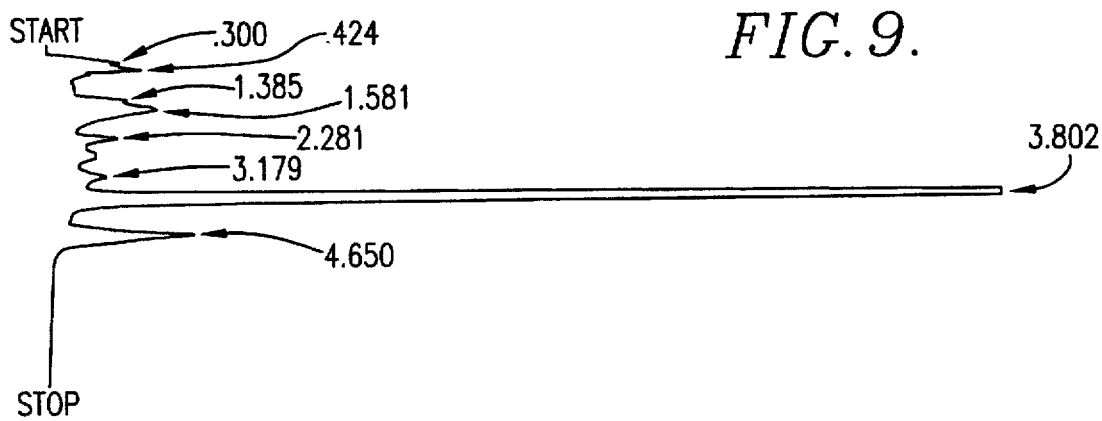
FIG. 9 shows an example of an individual sample report generated using the $A_2$ and F Quantitation method to analyze a patient's blood, wherein "NUM" refers to blood sample number, "RT" refers to absolute retention time, and "REL RT" refers to relative retention time.
FIG. 10 shows an example of a batch summary report generated using the $A_2$ and F Quantitation method to analyze patients' blood.

The $A_2$ and F Quantitation method was selected for quantitating only $A_2$ and F in the unknown blood samples from patients. This method was nearly identical to the High Resolution method. An individual sample report, an example of which is shown in FIG. 9, was printed after each sample run. However, for the unknown samples, only $A_2$ and/or F peaks were identified in the comment section. Additionally, the areas percent of F and $A_2$ were printed on a single line at the bottom of each report. Finally, a batch summary report, an example of which is shown in FIG. 10, was printed automatically at the conclusion of each batch run. Each batch summary report listed every sample which had been tested. The batch sample report included a) the sample number, b) the value of F, and c) the area percent value of $A_2$. An area percent value of $A_2$ greater than 10% was flagged with an error message indicating an invalid result due to the presence of a variant that comigrated with $A_2$.

Shutdown Method.

When the Shutdown method was selected, the system was automatically washed by passing a solution of 5% ethanol in water through the complete flow path, including the injector system, at a flow rate of 1.0 ml/minute for 10 minutes in order to remove buffer salts and other possible contaminants from the system. Additionally, the pumps, the lamp, and the column heater were turned off.

Computer Assistance.

The above-described steps and calculations were performed manually. However, they were preferably performed with the aid of the computer program set forth in detail in the attached Microfiche Appendix. The computer program operates a conventional microcomputer, minicomputer, or mainframe computer and is stored on a conventional computer-readable memory device such as a floppy or optical disk of the hard drive of the computer.

We claim:

1. A method for the identification of a hemoglobin variant in a blood sample comprising the steps of:
   (a) initially analyzing the blood sample by passing a first aliquot of the blood sample through an HPLC unit at a first resolution, and with a first eluant stream, eluting hemoglobin species, and characterizing the eluted species as a function of their respective absorbance values and retention times;
   (b) determining if an eluted species characterized at the first resolution has a characteristic indicative of a hemoglobin variant;
   (c) further analyzing the blood sample if an eluted species has a characteristic indicative of a hemoglobin variant by passing a second aliquot of the blood sample through an HPLC unit at a second resolution, and with a second eluant stream, eluting hemoglobin species, and characterizing the eluted species as a function of their respective absorbance values and retention times; and (d) comparing a characteristic of an eluted species characterized at the second resolution to characteristics of known hemoglobin variants to determine if the eluted species corresponds to a known hemoglobin variant, and wherein said HPLC unit is maintained at a temperature greater than 25° C. during said initial and further analyzing steps.

2. The method of claim 1, wherein the retention times are selected from the group consisting of absolute retention times and relative retention times.

3. The method of claim 2, wherein in step (b), an eluted species has a characteristic indicative of a hemoglobin variant if a chromatograph peak of the eluted species has a parameter value falling within a predetermined range of values.

4. The method of claim 3, wherein in step (b), an eluted species has a characteristic indicative of a hemoglobin variant if a chromatograph peak of the eluted species:

(a) is not an $A_0$ or $A_{1c}$ peak and has an area percent value greater than 5%;

(b) appears in the $A_{1c}$ window and has an area percent value greater than 10%;

(c) appears in the $A_0$ window and has an area percent value less than 80%;

(d) appears in the $A_0$ window and has a width greater than 1.2 times the width of the marker $A_0$ peak;

(e) appears in the degradation products window and has an area percent value greater than 10%;

(f) appears after the $A_2$ window;

(g) appears in the hemoglobin Bart's window and has an area percent value greater than 1%; or (h) appears in the $A_2$ window and has an area percent value greater than 10%.

5. The method of claim 2, wherein in step (d), the relative retention time of an eluted species is compared to relative retention times of known hemoglobin variants to determine if the eluted species corresponds to a known hemoglobin variant.

6. The method of claim 5, wherein the known hemoglobin variant is a genetic variant.

7. The method of claim 6, wherein the genetic variant is selected from the group consisting of Barts, Acetyl F, H, Acetyl S, Florida, Hope, F, Camden, I, N. Baltimore, I. High Wycombe, J. Baltimore, Fannin Lubbock, S. Florida (peak 1), Westmead, S. Florida (peak 2), Chicago, Lepore Baltimore, Lepore Boston, P. Galveston, G. Couchatta, Zurich, E, Osu Christianborg, Korle Bu, Koln (peak 1), G. Philadelphia, D. Punjab, Russ, D. E. Saskatoon, Deer Lodge, S. Q. Thailand, Montgomery, $A_2$', Koln (peak 2), Q. India, G. San Jose, and Sealy (Hasharon).

8. The method of claim 1, wherein column of the HPLC unit is maintained at a temperature of from about 30° C. to 50° C.

9. The method of claim 1, wherein the flow rate of the first eluant stream is greater than 1.5 ml/minute.

10. The method of claim 9, wherein the flow rate of the first eluant stream is from about 2.5 ml/minute to 3.5 ml/minute.

11. The method of claim 1, wherein the flow rate of the second eluant stream is greater than 1.5 ml/minute.

12. The method of claim 11, wherein the flow rate of the second eluant stream is from about 2 ml/minute to 3 ml/minute.

13. The method of claim 1, wherein the method is conducted with the aid of a computer.

14. A method for the identification of hemoglobin variants in a plurality of blood samples comprising the steps of:

(a) initially analyzing a respective blood sample by passing a first aliquot of the respective blood sample through an HPLC unit at a first resolution, and with a first eluant stream, eluting hemoglobin species, and characterizing the eluted species as a function of their respective absorbance values and retention times;

(b) repeating step (a) to analyze each of the plurality of blood samples;

(c) determining if an eluted species from any of the plurality of blood samples and characterized at the first resolution has a characteristic indicative of a hemoglobin variant;

(d) further analyzing a respective blood sample if an eluted species from that blood sample has a characteristic indicative of a hemoglobin variant by passing a second aliquot of the respective blood sample through an HPLC unit at a second resolution, and with a second eluant stream, eluting hemoglobin species, and characterizing the eluted species as a function of their respective absorbance values and retention times;

(e) repeating step (d) to further analyze any of the plurality of blood samples if an eluted species from any of the plurality of blood samples has a characteristic indicative of a hemoglobin variant; and (f) comparing a characteristic of an eluted species characterized at the second resolution to characteristics of known hemoglobin variants to determine if the eluted species corresponds to a known hemoglobin variant, wherein the total time between successive steps (a) is from about 2–4 minutes.

15. The method of claim 14, wherein the total time between successive steps (a) is less than 20 minutes.

16. The method of claim 14, wherein the total time between successive steps (d) is less than 20 minutes.

17. The method of claim 16, wherein the total time between successive steps (d) is from about 8 minutes to 12 minutes.

18. The method of claim 14, wherein the method is conducted with the aid of a computer.

19. A method for the identification of hemoglobin variants in a plurality of blood samples comprising the steps of:

(a) analyzing a respective blood sample by passing it through an HPLC unit, and with an eluant stream, eluting hemoglobin species, and characterizing the eluted species as a function of their respective absorbance values and retention times; and (b) repeating step (a) to analyze each of the plurality of blood samples, wherein the total time between successive steps (a) is less than 20 minutes;

(c) determining if an eluted species from any of the plurality of blood samples has a characteristic indicative of a hemoglobin variant, wherein the total time between successive steps (a) is from about 2–4 minutes.

20. The method of claim 19, wherein the total time between successive steps (a) is from about 8 minutes to 12 minutes.

21. The method of claim 19, wherein the retention times are selected from the group consisting of absolute retention times and relative retention times.

22. The method of claim 21, wherein in step (c), an eluted species has a characteristic indicative of a hemoglobin variant if a chromatograph peak of the eluted species has a parameter value falling within a predetermined range of values.

23. The method of claim 22, wherein in step (c), an eluted species has a characteristic indicative of a hemoglobin variant if a chromatograph peak of the eluted species:

(a) is not an $A_0$ or $A_{1c}$ peak and has an area percent value greater than 5%;

(b) appears in the $A_{1c}$ window and has an area percent value greater than 10%;

(c) appears in the $A_0$ window and has an area percent value less than 80%;

(d) appears in the $A_0$ window and has a width greater than 1.2 times the width of the marker $A_0$ peak;

(e) appears in the degradation products window and has an area percent value greater than 10%;

(f) appears after the $A_2$ window;

(g) appears in the hemoglobin Bart's window and has an area percent value greater than 1%; or (h) appears in the $A_2$ window and has an area percent value greater than 10%.

24. The method of claim 21, wherein in step (c), a characteristic of an eluted species is compared to characteristics of known hemoglobin variants to determine if the eluted species corresponds to a known hemoglobin variant.

25. The method of claim 24, wherein in step (c), the relative retention time of an eluted species is compared to relative retention times of hemoglobin variants to determine if the eluted species corresponds to a known hemoglobin variant.

26. The method of claim 25, wherein the known hemoglobin variant is a genetic variant.

27. The method of claim 26, wherein the genetic variant is selected from the group consisting of Barts, Acetyl F, H, Acetyl S, Florida, Hope, F, Camden, I, N. Baltimore, I. High Wycombe, J. Baltimore, Fannin Lubbock, S. Florida (peak 1), Westmead, S. Florida (peak 2), Chicago, Lepore Baltimore, Lepore Boston, P. Galveston, G. Couchatta, Zurich, E, Osu Christianborg, Korle Bu, Koln (peak 1), G. Philadelphia, D. Punjab, Russ, D. E. Saskatoon, Deer Lodge, S, Q. Thailand, Montgomery, $A_2'$, Koln (peak 2), Q. India, G. San Jose, and Sealy (Hasharon).

28. The method of claim 19, wherein the method is conducted with the aid of a computer.

29. A method for the identification of a hemoglobin variant in a blood sample comprising the steps of:

(a) initially analyzing the blood sample by passing a first aliquot of the blood sample through an HPLC unit at a first resolution, and with a first eluant stream, eluting hemoglobin species, and characterizing the eluted species as a function of their respective absorbance values and retention times;

(b) determining if an eluted species characterized at the first resolution has a characteristic indicative of a hemoglobin variant;

(c) further analyzing the blood sample if an eluted species has a characteristic indicative of a hemoglobin variant by passing a second aliquot of the blood sample through an HPLC unit at a second resolution, and with a second eluant stream, eluting hemoglobin species, and characterizing the eluted species as a function of their respective absorbance values and retention times; and (d) comparing a characteristic of an eluted species characterized at the second resolution to characteristics of known hemoglobin variants to determine if the eluted species corresponds to a known hemoglobin variant, wherein the flow rates of said first and second eluant streams are greater than 1.5 ml/min.

30. The method of claim 29, wherein said first flow rate is from about 2.5–3.5 ml/min. and the flow rate of second eluant stream is from about 2–3 ml/min.

31. A method for the identification of hemoglobin variants in a plurality of blood samples comprising the steps of:

(a) initially analyzing a respective blood sample by passing a first aliquot of the respective blood sample through an HPLC unit at a first resolution, and with a first eluant stream, eluting hemoglobin species, and characterizing the eluted species as a function of their respective absorbance values and retention times;

(b) repeating step (a) to analyze each of the plurality of blood samples;

(c) determining if an eluted species from any of the plurality of blood samples and characterized at the first resolution has a characteristic indicative of a hemoglobin variant;

(d) further analyzing a respective blood sample if an eluted species from that blood sample has a characteristic indicative of a hemoglobin variant by passing a second aliquot of the respective blood sample through an HPLC unit at a second resolution, and with a second eluant stream, eluting hemoglobin species, and characterizing the eluted species as a function of their respective absorbance values and retention times;

(e) repeating step (d) to further analyze any of the plurality of blood samples if an eluted species from any of the plurality of blood samples has a characteristic indicative of a hemoglobin variant; and (f) comparing a characteristic of an eluted species characterized at the second resolution to characteristics of known hemoglobin variants to determine if the eluted species corresponds to a known hemoglobin variant, wherein the total time between successive steps (d) is from about 8–12 minutes.

32. In a chromatographic method for the identification of hemoglobin variants including the steps of injecting a blood sample into the column of an HPLC unit, separating different hemoglobin species from the blood sample, and individually analyzing the different hemoglobin species, the improvement which comprises separating the different hemoglobin species while maintaining the column at a temperature greater than 25° C.

33. The method of claim 32, wherein the temperature is from about 30° C. to 50° C.

34. In a chromatographic method for the identification of hemoglobin variants including the steps of injecting a blood sample into the column of an HPLC unit, separating different hemoglobin species from the blood sample, and individually analyzing the different hemoglobin species, the improvement which comprises separating the different hemoglobin species using an eluant flow rate of greater than 1.5 ml/minute.

35. The method of claim 34, wherein the eluant flow rate is from about 2 ml/minute to 3.5 ml/minute.

* * * * *